(12) United States Patent
Krause et al.

(10) Patent No.: US 9,901,531 B2
(45) Date of Patent: *Feb. 27, 2018

(54) COSMETIC COMPOSITION COMPRISING A THICKENING POLYMER HAVING HYDROPHOBIC AND HYDROPHILIC PORTIONS

(71) Applicant: Noxell Corporation, Hunt Valley, MD (US)

(72) Inventors: Thomas Krause, Darmstadt (DE); Silke Niesig, Gross-Bieberau (DE); Florian Haas, Liederbach (DE)

(73) Assignee: Noxell Corporation, Hunt Valley, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/740,333

(22) Filed: Jun. 16, 2015

(65) Prior Publication Data

US 2016/0008258 A1 Jan. 14, 2016

(30) Foreign Application Priority Data

Jun. 17, 2014 (EP) .................................... 14172670
Jul. 23, 2014 (EP) .................................... 14178122

(51) Int. Cl.
*A61Q 5/10* (2006.01)
*A61K 8/87* (2006.01)
(Continued)

(52) U.S. Cl.
CPC .................. *A61K 8/87* (2013.01); *A45D 7/04* (2013.01); *A61K 8/34* (2013.01); *A61K 8/345* (2013.01);
(Continued)

(58) Field of Classification Search
CPC . A61Q 5/06; A61Q 5/065; A61Q 5/10; A61Q 5/12; A61K 8/87; A61K 8/8164;
(Continued)

(56) References Cited

U.S. PATENT DOCUMENTS

| 4,195,972 A | 4/1980 | Lapidus |
| 5,384,118 A | 1/1995 | LaValle |

(Continued)

FOREIGN PATENT DOCUMENTS

| CN | 102973467 | 3/2013 |
| CN | 106456501 A | 2/2017 |

(Continued)

OTHER PUBLICATIONS

International Search Report and Written Opinion, PCT/US2015/035911, dated Sep. 14, 2015.

(Continued)

*Primary Examiner* — Eisa Elhilo
(74) *Attorney, Agent, or Firm* — Schwegman Lundberg & Woessner, P.A.

(57) ABSTRACT

A cosmetic composition comprising a thickening polymer having hydrophobic and hydrophilic portions, a non-ionic surfactant, a neutralizing agent, a non-ionic kosmotrope and water. Also, a hair colorant formulation obtained from mixing said composition and a hair dye. Also, the use of said formulation for coloring and/or sculpting hair.

15 Claims, 6 Drawing Sheets

(51) Int. Cl.
*A61Q 5/00* (2006.01)
*A61Q 5/02* (2006.01)
*A61Q 5/06* (2006.01)
*A61Q 5/12* (2006.01)
*A61K 8/81* (2006.01)
*A45D 7/04* (2006.01)
*A61K 8/34* (2006.01)
*A61K 8/41* (2006.01)
*A45D 7/00* (2006.01)

(52) U.S. Cl.
CPC .............. *A61K 8/41* (2013.01); *A61K 8/8147* (2013.01); *A61K 8/8164* (2013.01); *A61Q 5/00* (2013.01); *A61Q 5/02* (2013.01); *A61Q 5/06* (2013.01); *A61Q 5/065* (2013.01); *A61Q 5/10* (2013.01); *A61Q 5/12* (2013.01); *A45D 2007/001* (2013.01); *A45D 2007/002* (2013.01); *A61K 2800/4324* (2013.01); *A61K 2800/54* (2013.01); *A61K 2800/591* (2013.01)

(58) Field of Classification Search
CPC ........ A61K 8/8147; A61K 8/41; A61K 8/345; A61K 2800/591; A61K 2800/54; A61K 2800/4324; A61K 8/34; A45D 2007/001; A45D 2007/002
USPC ............................................ 8/405; 424/70.16
See application file for complete search history.

(56) References Cited

U.S. PATENT DOCUMENTS

| | | | |
|---|---|---|---|
| 2002/0076387 A1 | 6/2002 | Birkel et al. | |
| 2003/0049224 A1 | 3/2003 | Birkel | |
| 2005/0232886 A1* | 10/2005 | Walter | A61K 8/8117 424/70.11 |
| 2006/0051311 A1 | 3/2006 | Walter et al. | |
| 2006/0210507 A1* | 9/2006 | Laurent | A61K 8/046 424/70.7 |
| 2011/0168201 A1 | 7/2011 | Bureiko et al. | |
| 2012/0129937 A1 | 5/2012 | Issleib et al. | |
| 2012/0255573 A1* | 10/2012 | Wood | A61Q 5/04 132/205 |
| 2013/0061866 A1 | 3/2013 | Klingelmeyer | |
| 2013/0302267 A1 | 11/2013 | Peffly et al. | |

FOREIGN PATENT DOCUMENTS

| | | |
|---|---|---|
| DE | 102010030654 | 1/2011 |
| EP | 1473028 | 11/2004 |
| EP | 1787631 | 5/2007 |
| EP | 2343037 A1 | 7/2011 |
| JP | 2001019626 | 1/2001 |
| JP | 2002053436 | 2/2002 |
| JP | 2002193772 | 7/2002 |
| JP | 2002322021 | 11/2002 |
| JP | 2003040746 | 2/2003 |
| JP | 2005336126 | 12/2005 |
| JP | 2017518327 A | 7/2017 |
| WO | 2014164213 A1 | 10/2014 |
| WO | WO-2015195592 A9 | 12/2015 |

OTHER PUBLICATIONS

"European Application Serial No. 14178122.9, Communication Pursuant to Article 94(3) EPC dated Sep. 14, 2016", 2 pgs.
"European Application Serial No. 14178122.9, Communication Pursuant to Article 94(3) EPC dated Dec. 23, 2016", 3 pgs.
"European Application Serial No. 14178122.9, Extended European Search Report dated Dec. 9, 2014", 5 pgs.
"European Application Serial No. 14178122.9, Response filed Mar. 14, 2017 to Communication Pursuant to Article 94(3) EPC dated Dec. 23, 2016", 9 pgs.

* cited by examiner

COSMETIC COMPOSITION COMPRISING A THICKENING POLYMER HAVING HYDROPHOBIC AND HYDROPHILIC PORTIONS

FIELD OF THE INVENTION

Cosmetic composition comprising: a thickening polymer having hydrophobic and hydrophilic portions, a non-ionic surfactant, a neutralising agent, a non-ionic kosmotrope and water. Also, a hair colorant formulation obtained from mixing said composition and a hair dye. Also, the use of said formulation for colouring and/or sculpting hair.

BACKGROUND OF THE INVENTION

Hair colouring or dyeing involves the application of a hair dye onto hair which results in the colouration of hair fibres. Typically the hair colour is changed or 'freshened up'. In highlighting, a limited number of sections of the head of hair—typically a plurality of hair fibres from their route to tip—are dyed to a lighter hair colour, wherein the sections are spaced out at intervals such that undyed sections remain in-between. Lowlighting is a similar procedure wherein a darker-coloured dye is utilised instead. The hair can also be highlighted with other colours e.g. red and/or purple tones. The entire head of hair can be dyed using this method e.g. with 3 different hair colouring agents for a more striking look. The end result is normally increased appearance of texture and vibrancy of the hair. The dyeing can also be tailored to the final hairstyle in order to highlight certain aspects or draw attention away from other features. Subtle highlighting/lowlighting can give the impression of a slight lightening/darkening of the hair shade and results in a fresher look.

Highlighting (and lowlighting) typically employs the use of barrier means, such as foils, in order to prevent bundles of hair fibres intentionally treated with a hair colouring agent from contacting other hair fibres and thus transfer of the hair colouring agent onto hair fibres that were not intended to be coloured at all or intended to be coloured with a different dye. Coloured fibres when contacted with other hair fibres can transfer their dye onto these other fibres, which are then also dyed—this is sometimes known as 'staining'. Therefore, barrier means are used to wrap up each intentionally dyed bundle of hair fibres and thus separate it from the other hair fibres. The wrapped bundles are then typically left to develop for a period of time before the hair dye is rinsed out and the final cut and style carried out.

There is a need, however, for the consumer to feel more beautiful during the hair dyeing process—some consumers believe that it detracts from this when they have to spend a period of time in the hairdressing salon with their head covered in e.g. foil parcels. Moreover, there is a need for speeding up the process of dyeing hair. Furthermore, there is a need for providing the stylist with greater artistic and creative freedom, vis-à-vis the relationship of the hair colour and the final hairstyle, during the application of the dye and during the dye development time. There is also a need for reducing the use of solid barrier means e.g. foils, such as for environmental reasons e.g. reduction of waste. Furthermore, there is a need to provide the consumer with a means to highlight/lowlight their hair by themselves i.e. at home without the need for a stylist. There is, moreover, a need for further improvements to known hair dyeing methods that do not use solid barrier means, such as foils. Such further improvements include product stability improvements.

WO2013/039887A2 discloses a method for colouring hair (...) wherein the method does not comprise the application of a solid barrier means in order to separate the first plurality of coated hair fibre portions from the second plurality of hair fibre portions. WO2013/039887A2 mentions that: "the first and/or second composition comprises from about 0.6% to about 8% associative thickening polymer". US2003/0049224A1 discloses an aqueous hair treatment gel contains a combination of at least one itaconic acid monoester/acrylate copolymer and at least one non-ionic, anionic, zwitterionic or amphoteric hair-fixing polymer (abstract). Claim 2 of US2003/0049224A1 states that the copolymer is from 1.5 to 10 percent.

In summary, there is a need for providing improved methods resulting in increased efficiency, flexibility and freedom for the stylist. There is a need for the consumer to have an improved feeling of well-being and beautification during the entire process of hair colouring and not just after treatment, and for the process to be quicker. There is a need for the stylists to be able to envision, create and experiment with the final look at every stage throughout the colouring process. There is also a need for product stability improvements in such improved methods.

SUMMARY OF THE INVENTION

In a first aspect, the present invention relates to a cosmetic composition comprising: at least 12% thickening polymer having hydrophobic and hydrophilic portions; a non-ionic surfactant; a neutralising agent; a non-ionic kosmotrope; water; and wherein the ratio of thickening polymer having hydrophobic and hydrophilic portions to neutralising agent is from 10:1 to 60:1.

A second aspect relates to a hair colorant formulation obtained from mixing: the composition according to the first aspect; a hair dye.

A third aspect relates to a method of colouring hair comprising applying the hair colorant formulation according to the second aspect to human hair.

A fourth aspect relates to the use of the formulation according to the second aspect for colouring and/or sculpting hair.

A fifth aspect relates to the use of a combination of a neutralising agent and a non-ionic kosmotrope for stabilizing a hair colorant composition.

BRIEF DESCRIPTION OF THE DRAWINGS

FIG. 1A shows composition 1 from Table Z. A clear solution is depicted. FIG. 1B shows composition 3 from Table 1: a white, opaque and highly viscous composition is depicted. The arrow indicates a stiff peak from the composition due to its very high viscosity.

FIG. 2A shows hair colorant formulation [0]. Hair colorant formulation [0] is made using composition 0 (see Table Z below), which is a composition according to the present invention. FIG. 2B and FIG. 2C show hair colorant formulation [3]. FIG. 2C depicts the hair colorant formulation [3] after spreading on hair. The arrow points to an insoluble lump on a hair fibre.

DETAILED DESCRIPTION OF THE INVENTION

Definitions and General

In this document, including in all embodiments of all aspects of the present invention, the following definitions apply unless specifically stated otherwise. All percentages are by weight (w/w) of the total composition. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 25° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". All amounts as they pertain to listed ingredients are based on the active level ('solids') and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol, would fall within this scope.

"Molecular weight" or "M. Wt." or "MW" and grammatical equivalents mean the number average molecular weight.

"Viscosity" is measured at 25° C. using a HAAKE Rotation Viscometer VT 550 with cooling/heating vessel and sensor systems according to DIN 53019 at a shear rate of 12.9 $s^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Dry" or "substantially dry" means comprising less than 5%, less than 3% or, less than 2%, less than 1%, or about 0% of any compound or composition being in liquid form when measured at 25° C. at ambient conditions. Such compounds or compositions being in liquid form include water, oils, organic solvents and other wetting agents. "Anhydrous" means that the composition comprises less than 5%, less than 3% or, less than 2%, less than 1%, or about 0% water by total weight of the composition.

"Substantially free from" or "substantially free of" means less than about 1%, or less than 0.8%, or less than 0.5%, or less than 0.3%, or about 0%, by total weight of the composition or formulation.

"Hair" means mammalian keratin fibres including scalp hair, facial hair and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Proximal to the scalp" means that portion of an extended, or substantially straightened, hair shaft that is closer in distance to the scalp than to the end of the hair. Thus, about 50% of the hair fibre length would be considered proximal to the scalp, and about 50% of the hair fibre would be distal to the scalp. "z cm proximal to the scalp" means a distance "z" along the hair, with one endpoint being on or directly adjacent to the scalp, and the second endpoint being measured "z" centimeters along the length of the extended or substantially straightened hair.

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

An "associative thickening polymer" is a polymer that is based on a water-soluble polymer e.g. acrylate polymers, cellulose ethers or polyethylene glycol. These typically comprise sidechains that are capped with water-insoluble hydrophobic groups like fatty alcohols, for example. In an aqueous solution or in emulsion, these polymers form a network that increases the viscosity of the solution/emulsion. The water-soluble backbone polymer is dissolves in water. The hydrophobic caps are adsorbed onto the hydrophobic emulsion polymer particles, or they form micelle structures with hydrophobes from other polymers. As each associative thickening polymer contains at least two hydrophobic caps, the result is a three-dimensional network within the emulsion. This increases the viscosity. Mainly the high- and mid-shear viscosity is affected.

"Hairstyling polymer" means a hair-fixing polymer which forms a film on a surface i.e. a film-forming polymer. 'Hairstyling polymer' and 'film-forming polymer' are used interchangeably in the art. In the context of hair science, this surface is the surface of individual hair fibres or a plurality thereof. The hairstyling polymer causes the hair fibres to be glued together to build welds, which are effectively cross-links that provide the hold benefit. In concert, these welds form a 'hairnet' to provide hair hold and volume benefits to the consumer. When the net of welds is effectively formed, the hold and volume benefits can last all day and offer good resistance to environmental humidity.

Theory Behind and Advantages of the Invention

The inventors have answered the aforementioned needs by carefully selecting the specific combination of mutually compatible features such that the interaction therewith results in a cosmetic composition, formulation, method and use that provide the following benefits. Firstly, the cosmetic composition allows the stylist to tailor the hair colouring to the final hairstyle by creating the hairstyle during the application of the hair colouring agent. This ability is due to the sculptability and hold benefits afforded by the composition(s) as described herein when mixed with a hair dye and optionally developing formulation (e.g. comprising an oxidising agent). The stylist therefore has greater artistic freedom to envisage the final hairstyle and the hair colouring effects fitting optimally thereto. In addition, hold provided by the composition provides the stylist with security and self-confidence because the section of hair coloured can be put in a specific orientation or placed in a specific location and it remains in this orientation/location due to the hold power provided by the cosmetic composition of the present invention. The stylist is thus able to achieve a wide variety of complex hairstyles, which may or may not be related to the hairstyle result when the hair is dry and the salon visit is over. Employing the inventive composition saves waste because the use of solid barrier means e.g. aluminium foils, is not necessary, since the hold/sculptability provided by the composition creates sufficient separation. The lack of foils also means that the stylist can better see where he or she is applying the colouring agent (hair dye) and where this is in relation to the entire head of hair. When using the inventive composition the colour effect is also faster to achieve than with foils. It also provides an aesthetic improvement of the application process—a variety of hair styles can be created during the application of the hair colouring agent. Furthermore, the present method is easier for apprentice/trainee stylists to learn—highlighting with foils requires excellent technique and significant practice—whereas employing the cosmetic composition according to the present invention is much faster for them to learn. Moreover, the inventive composition provides a way for consumers to create simple high- or low-lights at home since use of foils at home can be impractical and difficult to apply with only one pair of hands.

The cosmetic composition according to the present invention is an improvement over previous compositions in that it comprises a neutralising agent, a non-ionic kosmotrope and the ratio of thickening polymer having hydrophobic and hydrophilic portions to neutralising agent is from 10:1 to 60:1. This improvement is inter alia because of easier application due to better spreadability (distribution) on hair. Stylist feedback from testing as well as technical indications show an improved spreading behaviour for the herein-described cosmetic composition that results in a more even application, more easily achieved multi-colour techniques, all whilst maintaining excellent separation power (lack of staining) for different dye shades.

Also, the improved resistance to agglomeration of the latex structure formed by the thickening polymer having hydrophobic and hydrophilic portions during exposure to temperatures below 5° C. helps to ensure to provide a useable product to the consumer during travel to the salon—particularly in colder countries. Certain specific properties of the non-ionic kosmotrope help to achieve this without trade-off on overall product benefit.

Firstly, an extensive hydrogen-bond interaction of the non-ionic kosmotrope with water molecules weaken the water-water interactions and prevent formation of large crystals, for example at low temperatures. These large crystals would compress the latex micelles at intersections and cause irreversible agglomeration. The resulting product may thus be difficult to use in certain environment conditions due to difficult dose-ability and/or insufficient dispersion in the mixture of hair dye and developing formulation. Homogeneity and full unfolding of the polymer network in an acceptable time period thus cannot be expected during the application process. Small ice crystals formed in the interspace of the latex-particles do not force agglomeration however since the micelles are not moved together under pressure. Small crystals are acceptable because they are formed as the mixture freezes but they remain between the latex droplets and keep the micelles suitably segregated from each other.

Secondly, in its secondary function as a solubiliser the non-ionic kosmotrope helps the hydrophilic part of the associative polymer to expand even more (favourably) and form smoother aggregates compared to the situation without non-ionic kosmotrope or low levels of non-ionic kosmotrope. These aggregates help to achieve the improved spreadability desired by customers.

In a third function, the non-ionic kosmotrope acts as a softener of any hydrophobic phase and helps to change the formulation consistency in an appropriate way. This optimised balance maintains the main benefit of the herein-described composition (prevent formation of large crystals) while increasing the performance during application.

Furthermore, partial neutralisation of the polymer latex increases the water compatibility of the thickening polymer molecules, which are now partially or even completely dispersed in the water phase. As these macro-molecules (sections thereof) are located in the interspace of the latex particles they will act as a mechanical buffer and prevent the micelles from getting too close such that they would agglomerate in the manner of a colloidal protection.

Besides the presence of polymer that interacts with the water solvent (i.e. the thickening polymer having hydrophobic and hydrophilic portions), it additionally disturbs the formation of large ice crystals and keeps the domains of ice small. So the dispersed thickening polymer having hydrophobic and hydrophilic portions boosts the effect of the non-ionic kosmotrope on the structure of the frozen cosmetic composition positively.

In summary, the present invention provides a cosmetic composition, and related aspects thereof, that is both more stable and provides improved performance.

The details of the features and preferred features of the invention are described hereinafter.

$1^{st}$ Aspect

The first aspect relates to a cosmetic composition, which may be referred to herein as the "cosmetic composition" or simply "composition".

In at least one embodiment, the cosmetic composition is for colouring hair. Indeed, it is intended that the cosmetic composition is advantageously used as a mix-in composition for altering the properties of a standard hair colorant formulation, which contains at least one hair dye. Thus, in at least one embodiment, the cosmetic composition is substantially free of hair dye or pigment. This is useful in that it leaves the stylist and/or consumer free to choose their preferred hair dye and/or pigment.

The cosmetic composition comprises at least 12% thickening polymer having hydrophobic and hydrophilic portions. Said "thickening polymer having hydrophobic and hydrophilic portions" may be referred to hereinafter as simply the "thickening polymer". In at least one embodiment, the thickening polymer is an associative thickening polymer. In at least one embodiment, the thickening polymer is capable of interacting with the hydrophilic phase and capable of undergoing hydrophobic-hydrophobic interactions. The cosmetic composition comprises water and thus the hydrophilic phase comprises water. In at least one embodiment, the thickening polymer is an associative thickening polymer and comprises hydrophobic moieties and hydrophilic moieties. In at least one embodiment, the associative thickening polymer is a non-ionic or anionic polymer. The hydrophobic and hydrophilic moieties are advantageous since they help the thickening polymer interact with any hydrophobic phase and hydrophilic phase. In at least one embodiment, the hydrophobic moieties of the associative thickening polymer are capable of interacting with themselves and with the hydrophobic phase of the first and/or second composition. In at least one embodiment, associative thickening polymer is a block copolymer comprising hydrophobic blocks and hydrophilic blocks. In at least one embodiment, the block copolymer is an ABA-triblock copolymer. In at least one embodiment, the block copolymer is a polyurethane copolymer. In at least one embodiment, the hydrophilic blocks of the block copolymer comprise fatty alcohols. In at least one embodiment, associative thickening polymer comprises hydrophobic moieties as, or on the end of, sidechains. In at least one embodiment, the hydrophobic moieties and/or hydrophobic blocks of the thickening polymer consist of carbon and hydrogen atoms. In at least one embodiment, the associative thickening polymer comprises hydrophobic moieties and these comprise a saturated hydrocarbon chain consisting of carbon and hydrogen atoms. The associative thickening polymer may comprise a hydrophilic backbone substituted with at least one hydrophobic sidechain. The hydrophobic sidechain is important since it aids the associative thickening polymer to interact with the hydrophobic phase. In at least one embodiment, the associative thickening polymer comprises a unit comprising an acrylate group and a sidechain capable of forming hydrophobic interactions, particularly a sidechain comprising a saturated hydrocarbon chain consisting of carbon and hydrogen atoms. In at least one embodiment, the acrylate group is derived from the polymerisation of vinyl groups. In at least one embodiment, the backbone comprises acrylate, itaconate and/or urethane groups. In at least one embodiment, the thickening polymer is an associative thickening polymer, or wherein the thickening polymer is acrylate-based. In at least one embodiment, the hydrophilic moieties comprise urethane units. In at least one embodiment, the associative thickening polymer is substituted with a hydrophobic sidechain comprising at least 10 carbon atoms, or from 12 to 24 carbon atoms. The hydrophobic sidechain may comprise at least 8 carbon atoms, or at least 10 carbon atoms, or from 10 to 30 carbon atoms, or from 15 to 25 carbon atoms, or from 18 to 20 carbon atoms.

In at least one embodiment, the associative thickening polymer is non-crosslinked. Crosslinks may be inter-strand crosslinks, although intra-strand crosslinks are also used in this field of cosmetics. A non-crosslinked polymer is useful because high levels of crosslinked polymers can make the formulation too thick.

In at least one embodiment, the thickening polymer is selected from the group consisting of: Acrylates/Ceteth-20 Itaconate Copolymers, Acrylates/Beheneth-25 Methacrylate Copolymers and polyurethane polymers. In at least one embodiment, the thickening polymer is an Acrylates/Ceteth-20 Itaconate Copolymer. In at least one embodiment, the thickening polymer is an Acrylates/Beheneth-25 Methacrylate Copolymer. Aculyn™ 28 from Dow Personal Care (Rohm and Haas) has the INCI name Acrylates/Beheneth-25 Methacrylate Copolymer. An Acrylates/Beheneth-25 Methacrylate Copolymer is a copolymer of the ester of methacrylic acid and Beheneth-25 (q.v.) and one or more monomers of acrylic acid, methacrylic acid, or one of their simple esters. Aculyn™ 28 is synthesized from acrylic acid, acrylate esters and a beheneth-20 methacrylate ester. In at least one embodiment, the thickening polymer is a polyurethane polymer, such as a Polyurethane-39 polymer. Polyurethane-39 is a copolymer of PEG-140 and hexamethylene diisocyanate end-capped with C12-14 Pareth-10, C16-18 Pareth-11, and C18-20 Pareth-11. In at least one embodiment, the thickening polymer is selected from the group consisting of: Acrylates/Ceteth-20 Itaconate Copolymers, Polyurethane-39 polymers, and mixtures thereof; or wherein the thickening polymer is an Acrylates/Ceteth-20 Itaconate Copolymer. Suitable thickening polymers may include: Luvigel® Star from BASF, Aculyn™ 28 from Dow Personal Care (Rohm and Haas), Structure® 3001 from Akzo Nobel and Structure® 2001 from Akzo Nobel.

The cosmetic composition comprises at least 12% thickening polymer having hydrophobic and hydrophilic portions. In at least one embodiment, the composition comprises from 13% to 50%, or from 14% to 50%, or from 15% to 50%, or from 16% to 40%, or from 17% to 30% thickening polymer having hydrophobic and hydrophilic portions. In at least one embodiment, the composition comprises from 12% to 60%, or from 15% to 55%, or from 18% to 50%, or from 20% to 40% thickening polymer having hydrophobic and hydrophilic portions.

The composition comprises a non-ionic surfactant. It is advantageous for the surfactant to be non-ionic because any charge or salt can cause precipitation of the thickening polymer having hydrophobic and hydrophilic portions. In at least one embodiment, the composition comprises from 0.001% to 5%, or from 0.01% to 3%, or from 0.01% to 1%, or from 0.05 to 1%, or from 0.1% to 0.5%, or from 0.1% to 0.3% non-ionic surfactant. In at least one embodiment, the non-ionic surfactant is a castor oil having polyethylene glycol ether groups or polypropylene glycol ether groups. In at least one embodiment, the polyethylene glycol ether groups are ethers of PEG-n groups, wherein n is an integer of from 2 to 12, or from 2 to 10, or from 3 to 8. It is advantageous to have a total M.Wt. of polyethylene glycol ether groups below about 400 Da in order for ease of mixing. In at least one embodiment, the polypropylene glycol ether groups are ethers of PPG-n groups, wherein n is an integer of from 2 to 60, or from 10 to 50, or from 20 to 40. In at least one embodiment, the polyethylene glycol ether groups or polypropylene glycol ether groups are selected from the group consisting of: PPG-4, PPG-6, PEG-5, PEG-6, PEG-8, and mixtures thereof. In at least one embodiment, the composition comprises PEG-40 Hydrogenated Castor Oil and/or PEG-60 Castor Oil and/or PEG-35 Castor Oil as non-ionic surfactant.

The composition comprises a neutralising agent. In at least one embodiment, the neutralising agent is non-volatile. In at least one embodiment, the neutralising agent is an alkali. In at least one embodiment, the neutralising agent is an organic amine. In at least one embodiment, the neutralising agent is selected from the group consisting of: aminomethyl propanol, ethanolamine, and mixtures thereof. In at least one embodiment, the neutralising agent is aminomethyl propanol Aminomethyl propanol is often referred to as AMP, as 2-amino-2-methyl-propan-1-ol, or 2-amino-2-methyl-1-propanol, or as isobutanol-2-amine. AMP contains 4 carbon atoms and has the structure:

In at least one embodiment, the composition comprises from 0.01% to 2%, or from 0.1% to 1%, or from 0.2% to 0.8%, or from 0.35% to 0.6%, or from 0.40% to 0.45% neutralising agent. In at least one embodiment, the ratio of thickening polymer having hydrophobic and hydrophilic portions to neutralising agent is from 20:1 to 50:1, or from 35:1 to 45:1.

The composition comprises a non-ionic kosmotrope. Non-ionic kosmotropes are highly soluble well-hydrated molecules with little tendency to aggregate, having no net charge and strongly hydrogen bond to water, and that stabilize the structure of macromolecules in solution. A particular advantage of the non-ionic kosmotrope is the retainment of the fluidity of the cosmetic composition at low temperatures. Indeed, the non-ionic kosmotrope is able to alter structure of the cosmetic composition such that it freezes with different structure compared to without non-ionic kosmotrope. In the context of the present cosmetic composition, the non-ionic kosmotrope has the advantage that it prevents the thickening polymer having hydrophobic and hydrophilic portions from ordering e.g. agglomerating. The hydrophilic portions of the thickening polymer are in a hydrophilic phase with the water. The non-ionic kosmotrope stabilizes this phase and thus the thickening polymer micelles are kept suspended in the hydrophilic phase and prevented from agglomerating. This, for example, may occur at low temperatures. For example, when the cosmetic composition is thawed after freezing, the non-ionic kosmotrope preserves the structure of the micelles during this process. In at least one embodiment, the non-ionic kosmotrope is a polyhydric alcohol. In at least one embodiment, the non-ionic kosmotrope is selected from the group consisting of: polyethylene glycol, ethylene glycol, propylene glycol, propane-1,2,3-triol, and mixtures thereof.

In at least one embodiment, the non-ionic kosmotrope is propane-1,2,3-triol. Propane-1,2,3-triol is also known as glycerine, glycerine and as glycerol, and it has the following structure:

In at least one embodiment, the composition comprises from 1% to 20%, or from 5% to 18%, or from 5% to 20%, or from 7% to 15%, or from 8% to 12% non-ionic kosmotrope. The amount of the non-ionic kosmotrope needs to be carefully selected in view of the use of the cosmetic composition. For example, when used in a hair colorant formulation, there is a potential for colour shift of the colour result expected to be provided by the dye precursors employed in case too much non-ionic kosmotrope is employed. In at least one embodiment, the composition is substantially free of 1,2-propylene glycol.

The composition comprises water. Water is useful because it provides a hydrophilic phase, which the hydrophilic portions of the thickening polymer having hydrophobic and hydrophilic portions can interact with. Water is also useful because it provides a fluid phase meaning that the composition can be in liquid form and therefore easily mixed with other fluids such as hair dyes. In at least one embodiment, the composition comprises from 50% to 85% water, or from 65% to 75% water.

In at least one embodiment, the composition comprises at least one preservative and/or a mixture of preservatives. In at least one embodiment, the composition comprises from 0.01% to 1% preservative, or from 0.1% to 0.5% preservative. In at least one embodiment, the preservative is selected from the group consisting of benzyl alcohol, phenoxyethanol, 1,3-bis(hydroxymethyl)-5,5-dimethylimidazolidine-2,4-dione, and mixtures thereof. In at least one embodiment, the composition comprises at least one preservative; and wherein the preservative is selected from the group consisting of benzyl alcohol, phenoxyethanol, and mixtures thereof; or wherein the preservative is a mixture of benzyl alcohol and phenoxyethanol. In at least one embodiment, the composition is substantially free of benzoate compounds. Benzoate compounds are not preferred in view of the potential for instability and/or precipitation of the composition. In at least one embodiment, the composition is substantially free of parabens. Parabens are not preferred by some consumers.

In at least one embodiment, the composition is substantially free of any polar alcohol. Polar alcohols are not advantageous in the composition in view the potential for precipitation (of the thickening polymer). In at least one embodiment, the composition is substantially free of any further polymer, or is substantially free of any film-forming polymer, hairstyling polymer or hair fixing polymer. In at least one embodiment, the composition is substantially free of any further thickening polymer, or is substantially free of any film-forming polymer or hair fixing polymer except for the thickening polymer having hydrophobic and hydrophilic portions. In at least one embodiment, the composition is substantially free of any further thickening agent. In at least one embodiment, the composition is substantially free of a hair colouring agent. In at least one embodiment, the composition is substantially free of oxidising agent.

Example Embodiments of the $1^{st}$ Aspect

At least one embodiment relates to a cosmetic composition comprising:
from 15% to 40% thickening polymer having hydrophobic and hydrophilic portions;
from 0.01% to 1% non-ionic surfactant;
from 0.1% to 1% neutralising agent;
from 5% to 15% non-ionic kosmotrope;
water;
and wherein the ratio of thickening polymer having hydrophobic and hydrophilic portions to neutralising agent is from 10:1 to 60:1.

At least one embodiment relates to a cosmetic composition consisting of: at least 12% thickening polymer having hydrophobic and hydrophilic portions; a non-ionic surfactant; a neutralising agent; a non-ionic kosmotrope; water; and optional ingredients selected from the group consisting of: perfumes, preservatives; stabilisers, pH adjusting agents, vitamins, amino acids, and wherein the ratio of thickening polymer having hydrophobic and hydrophilic portions to neutralising agent is from 10:1 to 60:1.

At least one embodiment relates to a cosmetic composition consisting of: at least 12% thickening polymer having hydrophobic and hydrophilic portions; a non-ionic surfactant; a neutralising agent; a non-ionic kosmotrope; water; perfume; and preservatives; and wherein the ratio of thickening polymer having hydrophobic and hydrophilic portions to neutralising agent is from 10:1 to 60:1. In at least one embodiment, the preservatives are selected from the group consisting of benzyl alcohol, phenoxyethanol, 1,3-bis(hydroxymethyl)-5,5-dimethylimidazolidine-2,4-dione, and mixtures thereof. In at least one embodiment, the composition is substantially free of benzoate compounds. Benzoate compounds are not preferred in view of the potential for instability and/or precipitation of the composition. In at least one embodiment, the composition is substantially free of parabens. Parabens are not preferred by some consumers.

$2^{nd}$ Aspect

The second aspect relates to a hair colorant formulation obtained from mixing: the composition according to the first aspect; and a hair dye. In at least one embodiment, the hair dye is a formulation comprising a hair colouring agent. In at least one embodiment, the hair colouring agent is selected from the group consisting of: direct dyes, oxidative dye compounds, and mixtures thereof.

In at least one embodiment, the hair colouring agent is a direct dye. In at least one embodiment, the direct dye is present in an amount of from 0.001% to 4%, or from 0.005% to 3%, or from 0.01% to 2%. The presence of a direct dye and the proportion thereof is useful in that it can provide or enhance colouring/dyeing, particularly with regard to intensity. In at least one embodiment, the direct dye is selected from the group consisting of: nitro dyes to provide a blue colour, nitro dyes to provide a red colour, nitro dyes to provide a yellow colour, quinone dyes, basic dyes, neutral azo dyes, acid dyes, and mixtures thereof. In at least one embodiment, the direct dye is a nitro dye to provide a blue colour. In at least one embodiment, the direct dye is a nitro dye to provide a red colour. In at least one embodiment, the direct dye is a nitro dye to provide a yellow colour. In at least one embodiment, the direct dye is a quinone dye. In at least one embodiment, the direct dye is a basic dye. In at least one embodiment, the direct dye is a neutral azo dye. In at least one embodiment, the direct dye is an acid dye. In at least one embodiment, the direct dye is selected from the group consisting of: Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 16, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl) butane-1-sulfonate, N,N-dimethyl-3-(4-(methylamino)-9,10-dioxo-4a,9,9a,10-tetrahydroanthracen-1-ylamino)-N-propylpropan-1-aminium bromide, Disperse Dyes such as Disperse Red 17, Disperse Violet 1, Disperse Red 15, Disperse Violet 1, Disperse Black 9, Disperse Blue 3, Disperse Blue 23, Disperse Blue 377, Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1,2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2,2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal.

In at least one embodiment, the hair colouring agent is an oxidative dye compound. In at least one embodiment, the hair dye comprises a hair colouring agent, wherein the hair colouring agent is an oxidative dye compound. In at least one embodiment, hair colorant formulation is obtained from mixing: the composition according to the first aspect; a hair dye comprising an oxidative dye compound; and an oxidising agent. The oxidative dye compound may be selected from the group consisting of: primary intermediates, couplers, and mixtures thereof. In at least one embodiment, the hair colouring agent is a mixture of at least one primary intermediate and at least one coupler. The oxidative dye compound may also be in the form of an oxidative stable direct dye. In at least one embodiment, the hair colouring agent is a mixture of at least one primary intermediate, at least one coupler and at least one oxidative stable direct dye. The oxidative dye compounds suitable for use herein, in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

Oxidative dye compounds are known in the art, and include aromatic diamines, aminophenols, aromatic diols and their derivatives (a representative but not exhaustive list of oxidation dye precursors can be found in Sagarin, "Cosmetic Science and Technology", "Interscience, Special Edn. Vol. 2 pages 308 to 310). Suitable oxidative dye compounds are also disclosed in CA2576189A1, which bears the publication date 11 Jun. 2007—in particular, from Table 1 dye combinations No. 1 to 2394, which span pages 49 to 238, are incorporated herein by reference. It is to be understood that the primary intermediates and couplers (also collectively known as oxidative dye precursors) detailed below are only by way of example and are not intended to limit the compositions and other aspects herein described. The primary intermediates and couplers may be used in the form of salts, for example sulfate salts.

In at least one embodiment, the primary intermediate is selected from the group consisting of: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino) phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, and mixtures thereof. In at least one embodiment, the primary intermediate is 2-methoxymethyl-1,4-benzenediamine, which has the advantage of an improved sensitisation profile. In at least one embodiment, the primary intermediate is 4,5-diamino-1-hexylpyrazole. In at least one embodiment, the 4,5-diamino-1-hexylpyrazole is used as a sulfate salt. In at least one embodiment, the primary intermediate is selected from the group consisting of: 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene and salts thereof such as chlorides, sulfates and hemisulfates in particular.

In at least one embodiment, the coupler is selected from the group consisting of: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl) diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methyl-naphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

In at least one embodiment, the hair dye comprises 5-amino-4-chloro-o-cresol and 2-methoxymethyl-1,4-diaminobenzene. In at least one embodiment, the hair dye comprises 2,6-diaminopyridine and 2-methoxymethyl-1,4-diaminobenzene. In at least one embodiment, the hair dye comprises 2,6-dihydroxyethylaminotoluene and 2-methoxymethyl-1,4-diaminobenzene. In at least one embodiment, the hair dye comprises 2-methoxymethyl-1,4-diaminobenzene and p-phenylenediamine and/or toluene-2,5-diamine.

In at least one embodiment, the primary intermediate(s) and coupler(s) are present in an amount of from 0.001% to 12%, or from 0.01% to 10%, or from 0.05% to 9%, or from 1% to 6%. In at least one embodiment, the hair dye is substantially free of a direct dye.

In at least one embodiment, the hair colorant formulation has a storage modulus of at least 3000 Pa, or at least 3300 Pa, or at least 3500 Pa, or at least 4000 Pa, or at least 4500 Pa, or at least 5000 Pa, measured by frequency sweep at an angular frequency of 0.6 rad/s at 23° C. In an embodiment, the hair colorant formulation has a storage modulus of at least 3000 Pa, or at least 3300 Pa, or at least 3500 Pa, or at least 4000 Pa, or at least 4500 Pa, or at least 5000 Pa, measured by frequency sweep at an angular frequency of 0.6 rad/s at 23° C.; and wherein the hair colorant formulation comprises from 12% to 25% thickening polymer having hydrophobic and hydrophilic portions.

In at least one embodiment, the hair colorant formulation is obtained from mixing together, at a certain ratio, a hair dye, a developing formulation, and the cosmetic composition according to the first aspect. In at least one embodiment, the weight ratio of the hair dye to the developing formulation (i.e. hair dye:developing formulation) is from 1:5 to 5:1. In at least one embodiment, the weight ratio of the hair dye to the developing formulation to the composition according to the first aspect (i.e. hair dye:developing formulation: composition according to the first aspect) is from 10:10:0.5 to 10:10:2, or from 10:20:0.5 to 10:20:2. For example, for natural blonde shades, typically a mixing ratio of 10:20:2 (i.e. hair dye:developing formulation:composition according to the first aspect) is usually used.

In at least one embodiment, the hair colorant formulation is obtained from mixing: the composition according to the first aspect; a hair dye comprising an oxidative dye compound; and an oxidising agent. In at least one embodiment, hair colorant formulation is obtained from mixing: the composition according to the first aspect; a hair dye comprising an oxidative dye compound; and a developing formulation.

In at least one embodiment, the developing formulation comprises an oxidising agent. The oxidizing agent may be present in an amount sufficient to bleach melanin pigment in hair and/or cause formation of dye chromophores from oxidative dye compounds (including primary intermediates and/or couplers, when present). In at least one embodiment, the developing formulation comprises from 0.1% to 20%, or from 0.5% to 12%, or from 1% to 10%, or from 3% to 10%, or from 5% to 10% oxidising agent. In at least one embodiment, the oxidising agent is present in an amount of from 0.1% to 20%, or from 1% to 10%, or from 2% to 5%, by total weight of the first composition or the second composition. Inorganic peroxygen materials capable of yielding hydrogen peroxide in an aqueous medium may be used. In at least one embodiment, the oxidising agent is selected from group consisting of: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, particularly sodium salts thereof), which may be incorporated as monohydrates, tetrahydrates, etc.; alkali metal bromates; enzymes; and mixtures thereof. In at least one embodiment, the oxidizing agent is a percarbonate (such as sodium percarbonate, ammonium percarbonate and potassium percarbonate). In at least one embodiment, the oxidizing agent is sodium percarbonate. In at least one embodiment, the developing formulation is substantially free of persulfate.

$3^{rd}$ Aspect

The third aspect relates to a method of colouring hair comprising applying the hair colorant formulation according to the second aspect to human hair. In at least one embodiment, the hair is subsequently sculpted. In at least one embodiment, the method comprises applying a first hair colorant formulation according to the second aspect to human hair following by applying a second hair colorant formulation according to the second aspect to the same head of hair, wherein the first and second hair colorant formulations differ in the colour result provided by the respective hair dye present in the respective hair colorant formulation. The present invention has the advantage in this regard in that the thickening polymer prevents staining of the hair fibres which were not intended to be dyed with one of the hair dyes.

$4^{th}$ Aspect

The fourth aspect relates to the use of the formulation of the second aspect for colouring and/or sculpting hair. At least one embodiment relates to the use of the formulation of the second aspect for colouring and/or sculpting hair, or for improved spreading on hair, or for improved distribution on hair.

$5^{th}$ Aspect

The fifth aspect relates to the use of the combination of a neutralising agent and a non-ionic kosmotrope for stabilizing a hair colorant composition. In at least one embodiment, the fifth aspect relates to the use of the combination of a neutralising agent and a non-ionic kosmotrope for stabilizing a thickening polymer having hydrophobic and hydrophilic portions. Suitable thickening polymers have already been described when describing the first aspect above. In at least one embodiment, the fifth aspect relates to the use of the composition of the first aspect for colouring hair.

$6^{th}$ Aspect

A sixth aspect of the present invention relates to a kit comprising a composition according to the first aspect and a hair dye. The components of the kit may be separately packaged, for example in separate sealed containers. In at least one embodiment, the kit further comprises a developing formulation comprising an oxidising agent.

Optional Ingredients and Features

The following section applies to the composition of the first aspect and/or the formulation according to the second aspect and/or the developing formulation as described herein and/or the hair dye.

A composition and/or formulation as described herein may comprise a radical scavenger, in a sufficient amount to reduce damage to the hair during an oxidative bleaching or colouring process. The radical scavenger is advantageously selected such that it is not an alkalising agent. The radical scavenger is a species that can react with a carbonate radical to convert the carbonate radical by a series of fast reactions to a less reactive species. In at least one embodiment, the radical scavenger is selected from the group consisting of: alkanolamines, amino sugars, amino acids, and mixtures thereof. In at least one embodiment, the radical scavenger is selected from the group consisting of: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan, and potassium, sodium and ammonium salts of the above, and mixtures thereof. In at least one embodiment, the radical scavenger compound is selected from the group consisting of: benzylamine, glutamic acid, imidazole, di-tert-butylhydroxytoluene, hydroquinone, catechol, and mixtures thereof.

A composition and/or formulation as described herein may comprise a chelant. In at least one embodiment, the composition/formulation comprises chelant in an amount sufficient to reduce the amount of metals available to interact with formulation components, e.g. oxidizing agents, more particularly peroxides. Chelants are also known as chelators and chelating agents. In at least one embodiment, the chelant is selected from the group consisting of: diamine-N,N'-dipolyacid, monoamine monoamide-N,N'-dipolyacid, and N,N'-bis(2-hydroxybenzyl)ethylenediamine-N,N'-diacetic acid chelants (e.g. EDDS (ethylenediaminedisuccinic acid)), carboxylic acids (e.g. aminocarboxylic acids), phosphonic acids (e.g. aminophosphonic acids), polyphosphoric acids (in particular straight polyphosphoric acids), salts and derivatives thereof, and mixtures thereof. In at least one embodiment, the chelant is ethylenediamine tetraacetic acid (EDTA) and/or editronic acid.

In at least one embodiment, a composition and/or formulation as described herein comprises a hydrophilic phase. The hydrophilic phase may be in the form of or comprise a cosmetically acceptable carrier, for example an aqueous cosmetically acceptable carrier. In at least one embodiment, the composition/formulation comprises a cosmetically acceptable carrier. In at least one embodiment, the composition/formulation comprises from 60% to 99.9%, or from 70% to 95%, or from 80% to 90% cosmetically acceptable carrier. In at least one embodiment, the cosmetically acceptable carrier comprises or consists of water. In at least one embodiment, the cosmetically acceptable carrier comprises a compound selected from the group consisting of: silicones such as volatile silicones, amino or non-amino silicone gums; organic compounds such as $C_2$-$C_{10}$ alkanes, acetone, methyl ethyl ketone, volatile organic $C_1$-$C_{12}$ alcohols, esters of $C_1$-$C_{20}$ acids and of $C_1$-$C_8$ alcohols such as methyl acetate, butyl acetate, ethyl acetate, and isopropyl myristate, dimethoxyethane, diethoxyethane, $C_{10}$-$C_{30}$ fatty alcohols such as lauryl alcohol, cetyl alcohol, stearyl alcohol, and behenyl alcohol; $C_{10}$-$C_{30}$ fatty acids such as lauric acid and stearic acid; $C_{10}$-$C_{30}$ fatty amides such as lauric diethanolamide; $C_{10}$-$C_{30}$ fatty alkyl esters such as $C_{10}$-$C_{30}$ fatty alkyl benzoates; hydroxypropylcellulose, and mixtures thereof. In at least one embodiment, the carrier comprises water, fatty alcohols, volatile organic alcohols, and mixtures thereof. In at least one embodiment, the cosmetically acceptable carrier is water.

In at least one embodiment, the composition/formulation comprises a pH modifier and/or buffering agent. The amount is sufficiently effective to adjust the pH of the composition/formulation. In at least one embodiment, the composition/formulation has a pH ranging from pH 3 to pH 13, or from pH 7 to pH 12, or to pH 11, or to pH 10, or to pH 9, or to pH 8. In at least one embodiment, the cosmetic composition of the first aspect has a pH of 7 to 9. In some embodiments, the pH range for the carbonate ion source as described herein below is from 8.5 to 9.5, or from 8.0 to 9.0. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, or is selected from the group consisting of: sodium hydroxide, sodium silicate, sodium meta silicate and ammonium carbonate, and acidulents such as inorganic and inorganic acids, e.g., phosphoric acid, acetic acid, ascorbic acid, citric acid or tartaric acid, hydrochloric acid, and mixtures thereof.

A composition and/or formulation as described herein may comprise an alkalising agent. Herein "alkalising agent" means a compound suitable for raising the pH to alkaline level, in particular to a pH of between pH 9 and pH 11. Generally, the most commonly used alkalising agent in the art is ammonia. Non-ammonia alkalising agents are also known to the person skilled in the art and are advantageous due to reduced olfactory stimulation—for example, alkanolamines such as monoethanolamine. In at least one embodiment, the composition/formulation comprises a non-ammonia alkalising agent selected from the group consisting of: monoethanolamine (MEA), sodium silicate, sodium meta silicate, diethanolamine, triethanolamine, monopropanolamine, dipropanolamine, tripropanolamine, 2-amino-2-methyl-1,3-propanediol, 2-amino-2-methyl-1-propanol (a.k.a. aminomethylpropanol, AMP), 2-amino-2-hydroxymethyl-1,3-propanediol, and mixtures thereof. Monoethanolamine or aminomethylpropanol (AMP) are commonly used in ammonia-free hair dye products and may be used as the sole alkalising agent or in combination with each other or other alkalising agents. Monoethanolamine is in particular advantageously used alone or in combination with other non-ammonia alkalising agent. A composition and/or formulation as described herein may comprise ammonia in addition to the non-ammonia alkalising agent, for example less than 0.5% ammonia. In at least one embodiment, the alkalising agent is monoethanolamine. In at least one embodiment, the composition/formulation comprises the alkalising agent monoethanolamine and an oxidative dye compound being 2-methoxymethyl-1,4-benzenediamine.

In at least one embodiment, the composition/formulation comprises preservatives. In at least one embodiment, the composition/formulation comprises benzyl alcohol and phenoxyethanol.

In at least one embodiment, all compositions and formulations of the present invention are substantially free of persulfate. In at least one embodiment, the present invention does not encompass or include bleaching the hair.

Examples

The following examples further describe and demonstrate embodiments within the scope of the present invention. The examples are given solely for the purpose of illustration and are not to be construed as limitations of the present invention. All stated amounts are percent solids calculated by w/w of the total composition;

TABLE 1

Example cosmetic compositions

| Cosmetic composition | a | b | c | d | e | f |
|---|---|---|---|---|---|---|
| Acrylates/Ceteth-20 Itaconate Copolymer [1] | — | 15 | — | 13 | — | 17.7 |
| Polyurethane-39 polymer [2] | — | — | 18 | — | 17 | — |
| Acrylates/Beheneth-25 Methacrylate Copolymer [3] | 17 | — | — | — | — | — |
| PEG-40 Hydrogenated Castor Oil [4] | 0.2 | 0.3 | 0.3 | 0.3 | 0.3 | 0.3 |
| Propane-1,2,3-triol (glycerin) | 5 | 12 | 5 | — | 20 | 10 |
| Ethylene glycol | 2 | — | 5 | — | — | — |
| Propylene glycol | — | — | — | 15 | — | — |
| 2-amino-2-methyl-1-propanol [5] | — | 0.80 | 0.45 | — | 0.40 | 0.43 |
| Ethanolamine | 0.6 | — | — | 0.6 | 0.05 | — |
| DMDM Hydantoin [6] | — | 0.5 | — | 0.7 | — | — |
| Benzyl Alcohol | 0.40 | 0.40 | 0.40 | 0.35 | 0.35 | 0.40 |
| Phenoxyethanol | 0.20 | 0.20 | 0.20 | 0.25 | 0.25 | 0.20 |
| Water | QSP | QSP | QSP | QSP | QSP | QSP |
| Total | 100% | 100% | 100% | 100% | 100% | 100% |
| Ratio* | 28.3 | 18.8 | 40.0 | 21.7 | 37.8 | 41.1 |

KEY:
[1] = Structure ® 3001 from Akzo Nobel;
[2] = Luvigel Star from BASF;
[3] = Aculyn ® 28 from Rohm & Haas;
[4] = Cremophor RH 410 from BASF in 10% water;
[5] = AMP-95 ® from Dow Chemical Company;
[6] = Nipaguard™ DMDMH (1,3-bis(hydroxymethyl)-5,5-dimethylimidazolidine-2,4-dione) from Clariant Personal Care;
*= this ratio is the weight ratio of thickening polymer having hydrophobic and hydrophilic portions to neutralising agent.

EXPERIMENTAL

Consistency and Hold Experiments

Hair colorant formulations as per Table W are created by mixing together the following components:
a developing formulation from Table X;
a hair dye from Table Y;
a composition from Table Z.

TABLE W hair colorant formulations

| Hair colorant formulation | Developing formulation (Table X) | Hair dye (Table Y) | Composition (Table Z) | Ratio* | Mixing ratio (parts by weight) X:Y:Z |
|---|---|---|---|---|---|
| [0] | III | A | 0 | 41:1 | 10:10:1 |
| [0]' | V | C | 0 | 41:1 | 10:10:1 |
| [1] | III | A | 1 | 0.07:1 | 10:10:1 |
| [1]' | V | C | 1 | 0.07:1 | 10:10:1 |
| [2] | III | A | 2 | 10.5:1 | 10:10:1 |
| [2]' | V | C | 2 | 10.5:1 | 10:10:1 |
| [3] | III | A | 3 | 1.95:1 | 10:10:1 |
| [3]' | V | C | 3 | 1.95:1 | 10:10:1 |
| [4] | III | A | 4 | 2.04:1 | 10:10:6 |
| [4]' | V | C | 4 | 2.04:1 | 10:10:6 |

KEY:
*= this ratio is the weight ratio of thickening polymer having hydrophobic and hydrophilic portions to neutralising agent in the composition from Table Z.

TABLE X developing formulations III and V

| Developing Formulation | Concentration of oxidising agent[§] | Other components[§] |
|---|---|---|
| III | 6% | Hydrophobic phase comprising cetearyl alcohol (2% to 6%); surfactant (0.6% to 0.8%); hydrophilic phase comprising water (93% to 97%) |
| V | 12% | |

KEY:
[§]= stated numbers are percent calculated by w/w of the developing formulation.

TABLE Y hair dyes A and C

| Hair dye | Colour result | Hair colouring agent | Dye and salt load | Alkalising agent | Other components[§] |
|---|---|---|---|---|---|
| A | black | Oxidative dye compounds | high dye load, high electrolyte | low ammonia and MEA | Hydrophobic phase comprising hydrophobic components (20% to 28%); hydrophilic phase comprising water (50% to 76%); surfactant (4% to 6%); and alkalising agent(s) (3% to 11%). |
| B | intense red shade | Oxidative dye compounds | Low concentration of pyrazole-type dye(s) | high ammonia | |
| C | neutral light blond | Oxidative dye compounds | low dye load | high ammonia | |
| D | Deep, chocolate brown | Oxidative dye compounds | medium dye load, medium electrolyte | medium ammonia | |

KEY:
[§]= stated numbers are percent calculated by w/w of the total hair dye.

TABLE Z compositions

| Composition | 0 | 1 | 2 | 3 | 4 |
|---|---|---|---|---|---|
| Acrylates/Ceteth-20 Itaconate Copolymer[1] | 17.7 | 0.03 | 4.5 | 17.7 | 3.0 |
| Vinylpyrrolidone/Vinylacetate Copolymer[2] | — | — | — | — | 8.0 |
| PEG-40 Hydrogenated Castor Oil[3] | 0.27 | 0.27 | 0.27 | 0.27 | 0.405 |
| Propane-1,2,3-triol (glycerin) | 10.00 | 10.00 | 10.00 | 10.00 | — |
| 1,2-propylene glycol | — | — | — | — | 3.6 |
| 2-amino-2-methyl-1-propanol[4] | 0.43 | 0.43 | 0.43 | 9.1 | 1.47 |
| Benzyl Alcohol | 0.40 | 0.40 | 0.40 | 0.40 | — |
| Phenoxyethanol | 0.20 | 0.20 | 0.20 | 0.20 | — |
| Euxyl ® PE 9010[5] | — | — | — | — | 0.44 |
| Disodium EDTA[6] | — | — | — | — | 0.13 |
| para-hydroxybenzoic acid (PHB) methylester | — | — | — | — | 0.20 |
| D-panthenol | — | — | — | — | 0.30 |
| 4-bis(polyethoxy)paraaminobenzoic acid polyethoxyethyl ester (PEG-25 PABA)[7] | — | — | — | — | 0.50 |
| Dyes | — | — | — | — | 0.003 |
| Perfume | — | — | — | — | 0.35 |
| Distilled water | QSP | QSP | QSP | QSP | QSP |
| Total | 100% | 100% | 100% | 100% | 100% |

KEY:
[1]= Structure ® 3001 from Akzo Nobel;
[2]= Luviskol ® VA64 Powder from BASF;
[3]= Cremophor RH 410 from BASF plus 10% water;
[4]= AMP-95 ® from Dow Chemical Company (95% in water);
[5]= from Schülke - phenoxyethanol and ethylhexyglycerin;
[6]= Edeta ® BD from BASF;
[7]= Uvinul ® P25 from BASF.

Figure 1A:
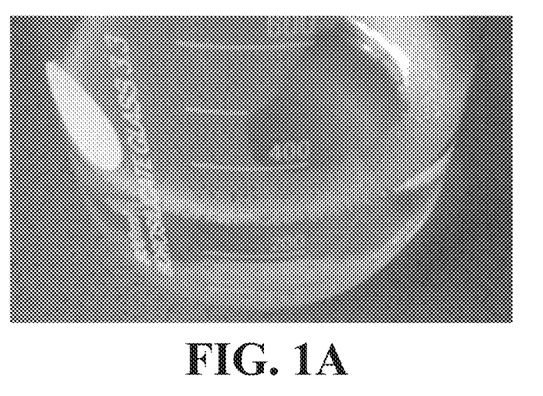
FIGS. 1A and 1B: Consistency of the compositions as created as per the Experimental section below. The compositions are show in a transparent glass beaker.
Figure 1B:
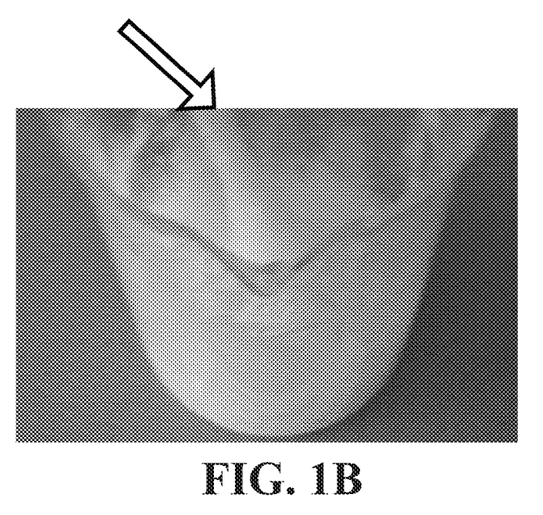
Figure 5:
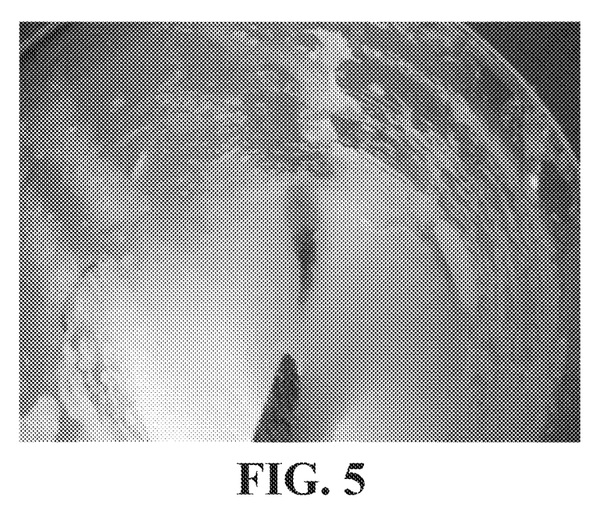
FIG. 5: The same composition as per FIG. 1B. The composition is so viscous it can be cut with a knife.

In the consistency and hold experiments, the compositions according to Table Z are tested to see if they can be mixed with, for example a hair dye. In particular, the viscosity, mixability and consistency of the compositions is evaluated. Selected photographs from this assessment are depicted in FIGS. 1A, 1B, and 5. Also, the viscosity, mixability and consistency of the hair colorant formulations according to Table W are evaluated. Their ability to impart hold on a hair tress is also considered. Selected photographs from these assessments are depicted in FIGS. 2A, 2B, 2C, 3, and 6.

FIG. 1A shows composition 1 from Table Z and a clear solution is depicted. The solution is highly fluid and runny i.e. has low viscosity. Composition 1 comprises a very low amount of thickening polymer having hydrophobic and hydrophilic portions.

FIG. 1B shows composition 3 from Table 1 and a white, opaque and highly viscous composition is depicted. The arrow indicates a stiff peak from the composition due to its very high viscosity. In FIG. 5 the same composition as per FIG. 1B is depicted. The composition is so viscous it can be cut with a knife.

Figure 2A:
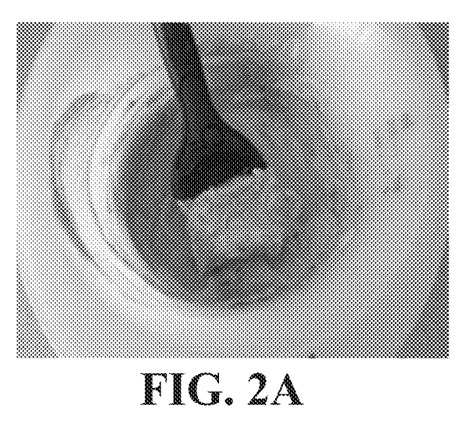
FIGS. 2A, 2B, and 2C: Consistency of the hair colorant formulations as created as per the Experimental section below—see Table W. The formulations shown in FIGS. 2A and 2B are in a plastic measuring cylinder.
Figure 2B:
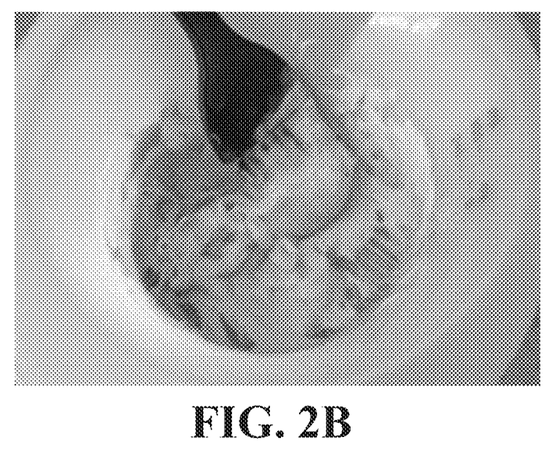
Figure 2C:
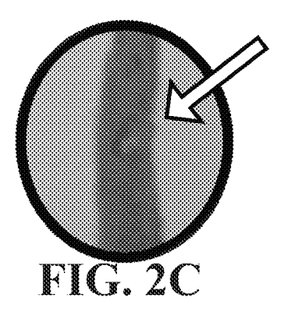

In FIG. 2 the consistency of the hair colorant formulations as created as per Table W is observed. The formulations shown in FIGS. 2A and B are photographed in a plastic measuring cylinder. FIG. 2A shows hair colorant formulation [0]. Hair colorant formulation [0] is made using composition 0 (see Table Z below), which is a cosmetic composition according to the present invention. FIG. 2A shows excellent hair colorant formulation consistency—the mixture is easily created and excellent application onto a hair tress is possible. FIG. 2B and FIG. 2C show hair colorant formulation [3]. Mixing hair colorant formulation [3] is difficult and insoluble lumps result. FIG. 2C depicts the hair colorant formulation [3] after spreading on hair and the arrow points to an insoluble lump on a hair fibre. These lumps are unacceptable and the hair colorant formulation is not appropriate to be used on head in view of likely unevenness of the colour result and highly concentrated areas of actives.

Figure 3:
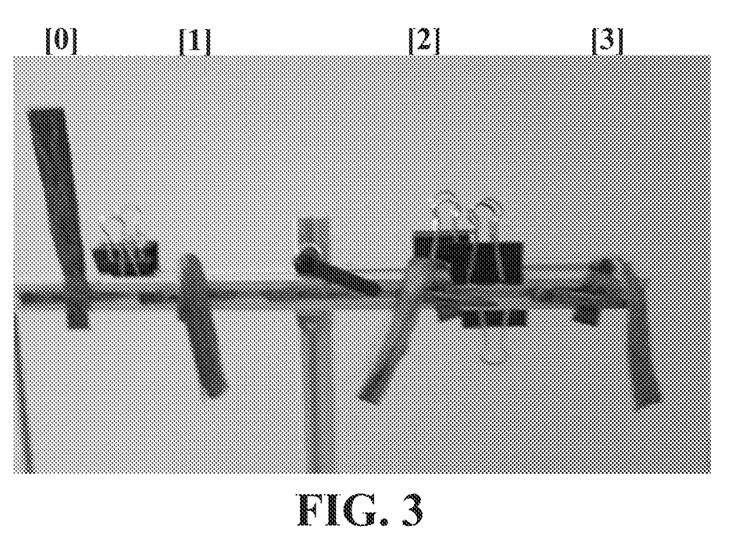
FIG. 3: The hold effect of the hair colorant formulations on hair tresses is shown. Four hair tresses are depicted in the photograph. These tresses have been coated in a hair colorant formulation as described in Table W. The hair colorant formulation used is indicated directly above the photograph in line with the fixing point of the hair tress to the stand. The tresses were initially fixed to the stand such that the hair fibres were pointing upwards and then allowed to enjoy the effects of gravity.

FIG. 3: The hold effect of the hair colorant formulations on hair tresses is shown. Four hair tresses are depicted in the photograph. These tresses have been coated in a hair colorant formulation as described in Table W. The hair colorant formulation used is indicated directly above the photograph in line with the fixing point of the hair tress to the stand. The tresses were initially fixed to the stand such that the hair fibres were pointing upwards and then allowed to enjoy the effects of gravity. Only hair colorant formulation [0] provides acceptable hold since it is more less still pointing upwards vertically whereas the other three hair colorant formulations i.e. [1] to [3], are pointing downwards indicating low hold and thus unacceptably low sculptability of the hair.

Figure 4:
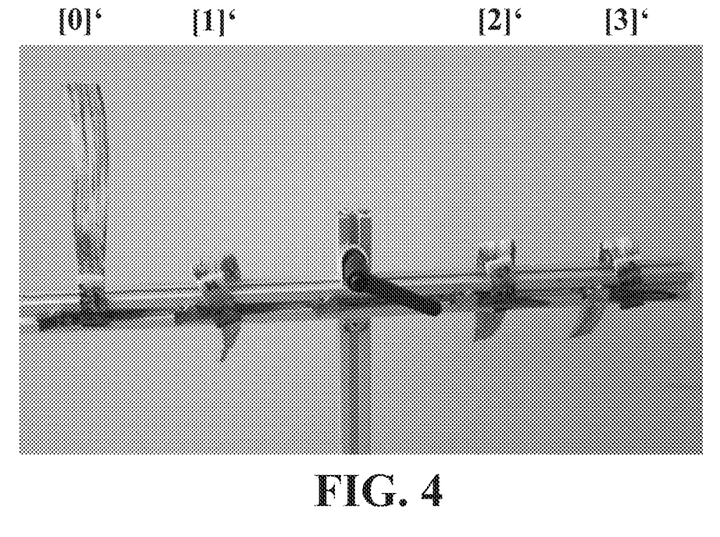
FIG. 4: The same experiment as per FIG. 3 except that different hair colorant formulations from Table W are used.

FIG. 4 depicts the results of the same experiment as per FIG. 3 except that different hair colorant formulations from Table W are used. The hair colorant formulations employed differ from those of FIG. 3 only in that a different hair dye is used. In FIG. 3, black hair dye is used whereas in FIG. 4 blonde hair dye is used. The results are the same as in FIG. 3 i.e. only hair colorant formulation [0]' provides acceptable hold since it is more less still pointing upwards vertically whereas the other three hair colorant formulations i.e. [1]' to [3]', are pointing downwards indicating low hold and thus unacceptably low sculptability of the hair.

Figure 6:
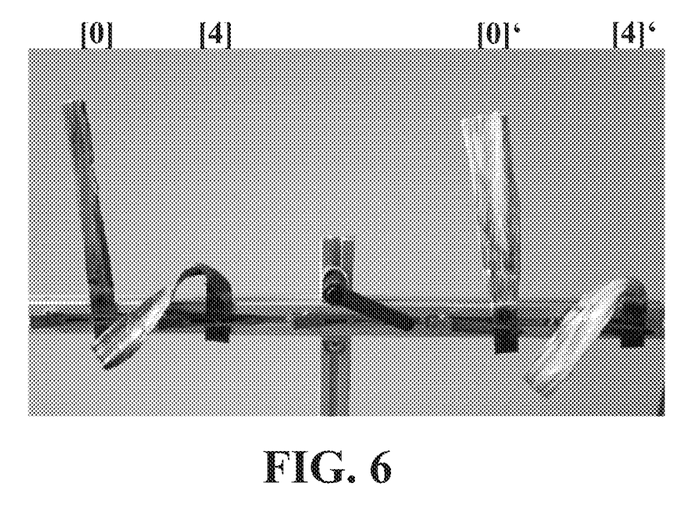
FIG. 6: The same experiment as per FIG. 3 except that different hair colorant formulations from Table W are compared.

FIG. 6 depicts the results of the same experiment as per FIG. 3 except that different hair colorant formulations from Table W are compared. In this figure, compositions 0 and 4 are compared in the context of hair colorant formulations [0] versus [4] and [0]' versus [4]'. In hair colorant formulations [0] and [4], a black hair dye is used, whereas in [0]' and [4]' a blonde hair dye is used. Compositions 0 and 4 differ from each other in that significantly more (about 6× more) thickening polymer having hydrophobic and hydrophilic portions is employed in the former versus the latter. Furthermore, a film-forming polymer is used in the latter composition verus the former composition.

Conclusions

The composition comprising a high level of Acrylates/Ceteth-20 Itaconate Copolymer but where the Acrylates/Ceteth-20 Itaconate Copolymer is fully neutralized (i.e. composition 3 in Table Z) is almost completely solid in consistency. It displays some visco-elastic properties i.e. is able to be stretched into peaks, but takes a long time to flow. When mixed with hair dye and developing formulation, it is lumpy.

These Data are Confirmed by Quantitative Experiments (Data not Shown).

Colour Shift Experiments

Compositions 0 and 4 are also compared, once mixed into a hair colorant formulation, in terms of the effect on the final colour result. These experiments are referred to herein as Colour Shift Experiments. In these experiments, hair dyes B and D are employed. This is because the end colour result that is provided by these hair dyes is sensitive to the ingredients used. Developing formulation III is used in all cases.

Data

TABLE I

Developing formulation from Table X = III; hair dye from Table Y = D; Composition from Table Z = 4.

| Hair swatch: | L* | a* | b* |
|---|---|---|---|
| Light brown | 15.75 | 4.95 | 3.72 |
| Natural blonde | 27.82 | 7.88 | 9.99 |

TABLE II

Developing formulation from Table X = III; hair dye from Table Y = D; Composition from Table Z = 0.

| Hair swatch: | L* | a* | b* |
|---|---|---|---|
| Light brown | 19.47 | 4.88 | 4.43 |
| Natural blonde | 22.29 | 7.35 | 7.25 |

TABLE III

Comparison of Table I versus Table II.

| Hair swatch: | Delta $E_{2000}$ |
|---|---|
| Light brown | 1.41 |
| Natural blonde | 2.87 |
| Average | 2.14 |

Therefore, the average colour result for light brown and natural blonde swatches differs on average by 2.14 when composition 4 is used versus composition 0.

The same experiments are carried out, but using a different hair dye from Table Y.

TABLE IV

Developing formulation from Table X = III; hair dye from Table Y = B; Composition from Table Z = 4.

| Hair swatch: | L* | a* | b* |
|---|---|---|---|
| Light brown | 19.22 | 11.96 | 7.12 |
| Natural blonde | 25.89 | 27.49 | 14.00 |

TABLE V

Developing formulation from Table X = III; hair dye from Table Y = B; Composition from Table Z = 0.

| Hair swatch: | L* | a* | b* |
|---|---|---|---|
| Light brown | 19.44 | 11.16 | 5.49 |
| Natural blonde | 24.95 | 25.49 | 11.27 |

TABLE VI

Comparison of Table IV versus Table V.

| Hair swatch: | Delta $E_{2000}$ |
|---|---|
| Light brown | 1.29 |
| Natural blonde | 1.75 |
| Average | 1.52 |

Therefore, the average colour result for light brown and natural blonde swatches differs on average by 1.52 when composition 4 is used versus composition 0.

Conclusions from Colour Shift Experiments

For the colours exhibited, the average Delta $E_{2000}$ is considered an unacceptable colour shift when the value is about 1.2. Thus, for both hair dye D and hair dye B, an unacceptable colour shift is visible and measurable for the natural blond swatch and for the light brown swatch. In other words, when composition 4 is used versus composition 0, an unacceptable colour shift is visible and measurable.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition comprising:
   at least about 12% thickening polymer having hydrophobic and hydrophilic portions;
   a non-ionic surfactant;
   a neutralising agent;
   a non-ionic kosmotrope;
   water;
   wherein the composition comprises at least one preservative; and
   wherein the preservative is selected from the group consisting of benzyl alcohol, phenoxyethanol, and mixtures thereof;
   wherein the non-ionic kosmotrope is propane-1,2,3-triol;
   wherein the composition comprises from about 0.01% to about 2% neutralising agent; and
   wherein the ratio of thickening polymer having hydrophobic and hydrophilic portions to neutralising agent is from about 10:1 to about 60:1.

2. The composition of claim 1, wherein the thickening polymer is an associative thickening polymer.

3. The composition of claim 2, wherein the thickening polymer is acrylate-based.

4. The composition of claim 1, wherein the composition comprises from about 15 to about 25% thickening polymer.

5. The composition of claim 4, wherein the composition also comprises from about 5% to about 20% non-ionic kosmotrope.

6. The composition of claim 1, wherein the thickening polymer is selected from the group consisting of Acrylates/Ceteth-20 Itaconate Copolymers, Polyurethane-39 polymers, and mixtures thereof.

7. The composition of claim 6, wherein the thickening polymer is an Acrylates/Ceteth-20 Itaconate Copolymer.

8. The composition of claim 1, wherein the neutralising agent is selected from the group consisting of: aminomethyl propanol, ethanolamine, and mixtures thereof.

9. The composition of claim 8, wherein the neutralising agent is aminomethyl propanol.

10. The composition of claim 1, wherein the composition comprises from about 0.2% to about 0.8% neutralising agent.

11. The composition of claim 10, wherein the ratio of thickening polymer having hydrophobic and hydrophilic portions to neutralising agent is from about 20:1 to about 50:1.

12. The composition according to claim 1, wherein the composition consists of:
    from about 15 to about 25% thickening polymer having hydrophobic and hydrophilic portions;
    a non-ionic surfactant;
    a neutralising agent;
    a non-ionic kosmotrope;
    water, and wherein the ratio of thickening polymer having hydrophobic and hydrophilic portions to neutralising agent is from about 10:1 to about 60:1.

13. A hair colorant formulation obtained from mixing:
    the composition according to claim 1;
    a hair dye.

14. A method of colouring hair comprising applying the hair colorant formulation according to claim 13 to human hair.

15. The method of claim 14 comprising sculpting hair.

* * * * *